(12) United States Patent
Schelges et al.

(10) Patent No.: US 10,085,934 B2
(45) Date of Patent: Oct. 2, 2018

(54) USE OF COSMETIC CLEANING COMPOSITIONS AS A PREBIOTIC

(71) Applicant: Henkel AG & Co. KGaA, Duesseldorf (DE)

(72) Inventors: Heike Schelges, Willich (DE); Elvira Scholz, Duesseldorf (DE); Stefanie Schmitz, Moenchengladbach (DE); Kirsten Sartingen, Brueggen (DE); Evelyn Domfeld, Duesseldorf (DE); Barbara Heide, Krefeld (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/376,204

(22) Filed: Dec. 12, 2016

(65) Prior Publication Data

US 2017/0087083 A1 Mar. 30, 2017

Related U.S. Application Data

(63) Continuation of application No. PCT/EP2015/061957, filed on May 29, 2015.

(30) Foreign Application Priority Data

Jun. 12, 2014 (DE) .................. 10 2014 211 204

(51) Int. Cl.
| | | |
|---|---|---|
| *A61K 8/98* | (2006.01) | |
| *A61K 8/64* | (2006.01) | |
| *A61K 8/36* | (2006.01) | |
| *A61K 8/34* | (2006.01) | |
| *A61K 8/49* | (2006.01) | |
| *A61K 8/81* | (2006.01) | |
| *A61K 8/97* | (2017.01) | |
| *A61Q 19/10* | (2006.01) | |

(52) U.S. Cl.
CPC .............. *A61K 8/986* (2013.01); *A61K 8/345* (2013.01); *A61K 8/361* (2013.01); *A61K 8/4926* (2013.01); *A61K 8/64* (2013.01); *A61K 8/817* (2013.01); *A61K 8/97* (2013.01); *A61Q 19/10* (2013.01)

(58) Field of Classification Search
None
See application file for complete search history.

(56) References Cited

U.S. PATENT DOCUMENTS

| | | | | |
|---|---|---|---|---|
| 5,928,631 A | * | 7/1999 | Lucas ...................... | A61K 8/19 422/5 |
| 2005/0123488 A1 | * | 6/2005 | Brautigam ............. | A61K 8/046 424/47 |
| 2005/0152863 A1 | * | 7/2005 | Brautigam ............. | A61K 8/986 424/70.1 |
| 2006/0276369 A1 | | 12/2006 | Levecke et al. | |
| 2009/0081149 A1 | * | 3/2009 | Watkins ................. | A61K 8/645 424/74 |
| 2009/0220444 A1 | | 9/2009 | Teckenbrock et al. | |
| 2009/0252812 A1 | * | 10/2009 | Lieurey .................. | A61K 8/986 424/535 |

FOREIGN PATENT DOCUMENTS

| | | |
|---|---|---|
| DE | 19534371 C1 | 2/1997 |
| DE | 102009002262 A1 | 10/2010 |
| WO | 2007/057080 A1 | 5/2007 |
| WO | WO 2008068656 A2 * | 6/2008 .............. A61K 8/42 |
| WO | WO 2008110942 A1 * | 9/2008 ............. A61K 8/986 |
| WO | 2010/115813 A1 | 10/2010 |
| WO | 2013/064403 A1 | 5/2013 |

OTHER PUBLICATIONS

WO 2013064403 English translation.*
PCT International Search Report (PCT/EP2015/061957) dated Jul. 23, 2015.

* cited by examiner

*Primary Examiner* — Christopher R Tate
*Assistant Examiner* — Douglas F White
(74) *Attorney, Agent, or Firm* — James J. Cummings

(57) ABSTRACT

A composition that includes spray-dried yoghurt powder and at least one anionic surfactant and/or at least one fatty acid soap, may be used as a prebiotic for inhibiting the growth and/or the physiological activity of undesired skin bacteria and/or for obtaining desired skin bacteria. A prebiotically effective cosmetic composition includes: a) at least one fatty acid soap in a weight proportion of between 20 and 75 wt. %, preferably between 30 and 70 wt. %, particularly preferably between 40 and 65 wt. %, and in particular between 45 and 60 wt. %; and b) spray-dried yoghurt powder in a weight proportion of between 0.01 and 10 wt. %, preferably 0.02 and 7.5 wt. %, particularly preferably between 0.03 and 5 wt. %, and in particular between 0.05 and 3 wt. %, wherein the amounts relate to the total weight of the cosmetic composition.

6 Claims, 1 Drawing Sheet

USE OF COSMETIC CLEANING COMPOSITIONS AS A PREBIOTIC

FIELD OF THE INVENTION

The present invention generally relates to cosmetics, and more particularly relates to the cosmetic, non-therapeutic use of a cosmetic composition as a prebiotic for inhibiting the growth and/or the physiological activity of undesirable skin microbes and/or for preserving desirable skin microbes.

The invention further relates to such a prebiotically active cosmetic composition.

BACKGROUND OF THE INVENTION

A multitude of different bacteria reside on the human skin surface, some of which must be considered harmful since they can cause skin diseases such as acne (known as "pathogenic bacteria"). Other skin microbes, in turn, provide a positive action (known as "saprophytic bacteria"), as growth of these is able to inhibit the reproduction of harmful bacteria, and as a result they exert a protective function on the skin. It is therefore desirable to influence the skin flora to the effect that the growth of pathogenic bacteria is reduced, and the growth of saprophytic bacteria is favored. Cosmetic cleansing agents usually include surfactants and/or surfactant combinations, which due to the irritating effect can adversely influence the skin flora and are therefore not recommended for use on blemished skin and/or skin suffering from acne. In the case of soaps, additionally the alkaline pH value can adversely influence the skin, which may worsen the skin complexion, especially in the case of skin imperfections.

DE 102009002262 already disclosed the use of prebiotically active surfactant combinations, in particular in washing and cleaning agents for hard surfaces. For cosmetic use on particularly sensitive parts of the skin, such as the facial skin, or for cosmetic use on diseased skin, however, milder compositions are desirable, which not only promote the growth and/or the viability of saprophytic bacteria of the skin flora as compared to the growth and/or the viability of pathogenic bacteria of the skin flora selectively at the application site (of the skin), but also ensure gentle cleansing of the skin and outstanding skin care.

It is therefore desirable to find substances or substance mixtures that exhibit a prebiotic action on the skin or in the skin flora and that are suitable for use in mild, nourishing skin cleansing preparations.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A method of using a composition, including spray-dried yoghurt powder and at least one anionic surfactant and/or at least one fatty acid soap, as a prebiotic for inhibiting the growth and/or the physiological activity of undesirable skin bacteria and/or for preserving desirable skin bacteria.

A prebiotically active cosmetic composition includes at least one fatty acid soap in a weight fraction of 10 to 75 wt. %, preferably 15 to 70 wt. %, particularly preferably 20 to 65 wt. %, and in particular 25 to 60 wt. %; and spray-dried yoghurt powder in a weight fraction of 0.01 to 10 wt. %, preferably 0.02 to 7.5 wt. %, particularly preferably 0.03 to 5 wt. %, and in particular 0.05 to 3 wt. %, wherein the quantity information is based on the total weight of the cosmetic composition.

BRIEF DESCRIPTION OF THE DRAWINGS

The present invention will hereinafter be described in conjunction with the following drawing figures.

DETAILED DESCRIPTION OF THE INVENTION

Figure 1:
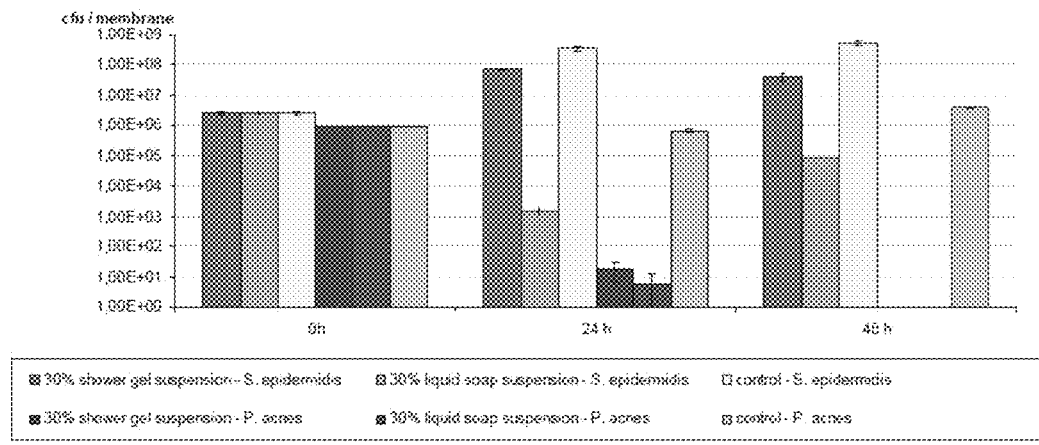
FIG. 1 is a bar graph depicting data for the prebiotic efficacy of a shower gel according to the present invention, and a liquid soap formulation according to the present invention, compared to a control (water)

The following detailed description of the invention is merely exemplary in nature and is not intended to limit the invention or the application and uses of the invention. Furthermore, there is no intention to be bound by any theory presented in the preceding background of the invention or the following detailed description of the invention.

One subject matter of the present invention is the cosmetic, non-therapeutic use of a cosmetic composition, comprising spray-dried yoghurt powder and at least one anionic surfactant and/or at least one fatty acid soap, as a prebiotic for inhibiting the growth and/or the physiological activity of undesirable skin microbes and/or for preserving desirable skin microbes.

Surprisingly, it was found that the combination of the spray-dried yoghurt powder and at least one anionic surfactant and/or at least one fatty acid soap forms an outstanding nourishing-cleansing complex, which can be used as a prebiotic in skin treatment agents, and in particular in skin cleansing agents.

A "prebiotic action" (or a prebiotic) according to the invention shall be understood to mean that the growth and/or the viability of the desirable, in particular friendly, skin bacteria or microflora as compared to the growth and/or the viability of the undesirable, in particular hostile, skin bacteria or microflora is promoted. This can be achieved not only in that the active ingredient and/or the active ingredient combination is conducive to the growth of the desirable skin bacteria, without directly influencing the growth of the undesirable skin bacteria, but also in that the active ingredient inhibits the growth of the undesirable skin bacteria, without directly influencing the growth of the desirable skin bacteria. In a particularly preferred and particularly surprising embodiment according to the invention, however, the active ingredient is conducive to the growth of the desirable skin bacteria, while inhibiting the growth of the undesirable skin bacteria.

According to the invention, the term "skin" shall preferably be understood to mean the skin itself, and in particular the human skin, but additionally also the mucosa and skin appendages, to the extent they comprise living cells, in particular hair follicles, hair roots, hair bulb, the ventral epithelial layer of the nail bed (lectulus), as well as sebaceous glands and sweat glands.

Inflammatory conditions of the skin are caused by harmful bacteria, such as *Propionibacterium acnes*, which permanently reside on the skin, but proliferate more drastically under certain conditions and cause "blemished skin" or acne, for example. These are essentially microorganisms (bacteria and fungi) that must be classified as pathogenic.

Antibacterial active ingredients, such as are used for preventing and controlling acne in commercially available cosmetics, for example, usually do not act selectively and not only kill undesirable skin bacteria, but also desirable skin bacteria and thereby disrupt the biological equilibrium, which can have a variety of undesirable consequences.

The use according to the invention does not have these disadvantages since it results in a selective elimination of undesirable skin bacteria, without adversely influencing the desirable skin bacteria. Moreover, the use according to the invention has the advantage that the skin is nourished, moisturized and soothed, which results in a general improvement of the complexion, especially in the case of blemished skin.

It was not to be expected that the active ingredient combination of spray-dried yoghurt powder and at least one fatty acid soap and/or the active ingredient combination of spray-dried yoghurt powder and at least one anionic surfactant exhibits the above-described prebiotic action in cosmetic compositions, since no prebiotic action is demonstrated for the individual components.

Particularly suited cosmetic compositions within the meaning of the present invention are preferably rinse-off products such as liquid or solid soaps, in particular syndets, shower gels, shower baths, facial toners, facial masks, facial washing gels and/or peeling products.

According to the invention, "spray-dried yoghurt powder" shall be understood to mean yoghurt powder obtainable from natural yoghurt (following complete fermentation) by way of lyophilization.
Particularly suited yoghurt powder for the use according to the invention preferably comprises the following main components:
- 40 to 65%, more preferably 45 to 60%, particularly preferably 50 to 55%, and in particular approximately 53.5% lactose;
- 20 to 30%, more preferably 22 to 28%, particularly preferably 24 to 26%, and in particular approximately 25% proteins;
- 5 to 10%, more preferably 6 to 9%, particularly preferably 7 to 8%, and in particular approximately 7.5% lactic acid;
- 1 to 10%, more preferably 2 to 8%, particularly preferably 4 to 60%, and in particular approximately 5% mineral nutrients and trace elements;
- 0.1 to 2%, more preferably 0.2 to 1.75%, particularly preferably 0.5 to 1.5%, and in particular approximately 1% vitamins;
- 0.5 to 5%, more preferably 1 to 4%, particularly preferably 1.5 to 3%, and in particular approximately 2% lipids,
wherein the quantity information is based on the total weight of the spray-dried yoghurt powder.

Spray-dried yoghurt powder is preferably used in the compositions to be used according to the invention in a weight fraction of 0.01 to 10 wt. %, more preferably 0.02 to 7.5 wt. %, particularly preferably 0.03 to 5 wt. %, and in particular 0.01 to 3 wt. %, wherein the quantity information is based on the total weight of the compositions.

In particular the spray-dried yoghurt powders available commercially by the designations "Yogurtene®" from Givaudan or "Yoghurt Protein GBU®" from Lipoid Kosmetik are suitable for the use according to the invention.

"Undesirable" bacteria within the meaning of the present invention shall be understood to mean preferably bacteria hostile to the skin and/or pathogenic bacteria and/or coagulase-positive bacteria, in particular *S. aureas*, or bacteria selected from the group consisting of *Propionibacterium acnes, Candida albicans, Malassezia furfir, Corynebacterium* spp. or *Peptostreptococcus* spp., in particular *Propionibacterium acnes*.

"Desirable" bacteria within the meaning of the present invention shall be understood to mean preferably harmless and/or not pathogenic and/or skin-friendly and/or saprophytic bacteria and/or coagulase-negative staphylococci, in particular *S. epidermidis, S. hominis, S warneri, S. saprophyticus, S. xylosus, S. capitis* or *S. simulans*, in particular *S. epidermidis* or *S. warneri*.

The prebiotically active cosmetic compositions to be used according to the invention are preferably conducive to the growth of coagulase-negative staphylococci, and in particular of *S. epidermidis* or *S. warneri*, while inhibiting the growth of *Propionibacterium acnes*.

A first preferred embodiment of the use according to the invention is thus characterized in that the prebiotically active cosmetic compositions are conducive to the growth of coagulase-negative staphylococci, and in particular of *S. epidermidis* or *S. warneri*, while inhibiting the growth of *Propionibacterium acnes*.

Possible application sites are the skin of any body region, in particular the facial skin, the scalp, the skin on the neck, décolleté, back, on the arms, in the axillary region and/or in the genital area. In a particularly preferred embodiment, the application site is the facial skin and/or the skin on the neck, décolleté, back and/or on the arms.

The use according to the invention of cosmetic compositions comprising spray-dried yoghurt powder and at least one fatty acid soap can be preferred according to the invention since it was found that the use of such a composition significantly promotes the growth of desirable skin bacteria (*S. epidermis*).

A second preferred embodiment of the use according to the invention is thus characterized in that the cosmetic compositions comprise spray-dried yoghurt powder and at least one fatty acid soap in a weight fraction of 10 to 75 wt. %, based on the total weight of the compositions.

"Fatty acid soaps" usually refer to the sodium, potassium or ammonium salts of fatty acids. "Fatty acids" shall be understood to mean linear and/or branched, saturated and/or unsaturated carboxylic acids having 6 to 30 carbon atoms, such as caproic acid, caprylic acid, 2-ethylhexanoic acid, capric acid, lauric acid, myristic acid, palmitic acid, stearic acid, arachidic acid and behenic acid, erucic acid, isostearic acid, isotridecanoic acid, but also elaidic acid, petroselinic acid, eleostearic acid, arachidic acid, gadoleic acid, palmitoleic acid, oleic acid, linoleic acid, linolenic acid and arachidonic acid. It is preferred to use technical mixtures, such as those obtainable from vegetable and animal fats and oils, for example from tallow fatty acids, coconut fatty acids, olive oil fatty acids, palm oil fatty acids, lard fatty acids and/or palm kernel oil fatty acids.

The sodium salts of the following fatty acids are particularly preferred for the use according to the invention: of tallow fatty acid (INCI name: Sodium Tallowate), of coconut fatty acid (INCI name: Sodium Cocoate), of olive oil fatty acid (INCI name: Sodium Olivate), of palm oil fatty acids (INCI name: Sodium Palmate), of lard fatty acids (INCI names: Sodium Lardate) and/or of palm kernel oil fatty acids (INCI name: Sodium Palm Kernelate).

The total amount of fatty acid soaps in the cosmetic compositions of the second preferred embodiment is preferably 10 to 75 wt. %, more preferably 15 to 70 wt. %, particularly preferably 20 to 65 wt. %, and in particular preferably 25 to 60%, wherein the quantity information is based on the total weight of the cosmetic compositions.

Within the second preferred embodiment, it is particularly preferred for the cosmetic composition to be present in the form of a solid, pasty or liquid soap or as a combar (mixture of syndet and soap).
Within this embodiment, the cosmetic composition preferably has a water content of
- no more than 20 wt. %, more preferably of no more than 18 wt. %, particularly preferably of no more than 16 wt. %, and in particular of no more than 15 wt. % (in the case of a solid soap), and
- at least 60 wt. %, more preferably 65 wt. %, particularly preferably 70 wt. %, and in particular 75 wt. % (in the case of a liquid soap),
- wherein the quantity information is based on the total weight of the cosmetic composition.

The use according to the invention of cosmetic compositions comprising spray-dried yoghurt powder and at least one anionic surfactant may likewise be preferred. It was found that using such a composition significantly inhibits the growth of undesirable skin bacteria (*Propionbacterium acnes*), while promoting the growth of desirable skin bacteria (*S. epidermis*).

The prebiotic efficacy and the mildness of the compositions were moreover enhanced with careful selection of the nature and amount of the at least one anionic surfactant.

The combination of at least one anionic surfactant with at least one amphoteric surfactant and/or zwitterionic surfactant has proven to be particularly advantageous.

The combination of at least one anionic surfactant with at least one cationic polymer has also proven to be particularly advantageous.

A third preferred embodiment of the use according to the invention is thus characterized in that the cosmetic compositions, in addition to spray-dried yoghurt powder, comprise
- a) at least one anionic surfactant in a weight fraction of 3 to 8 wt. %, and
- b) at least one amphoteric and/or zwitterionic surfactant in a weight fraction of 1 to 6 wt. %, wherein the quantity information is based on the total weight of the compositions.

Within this embodiment, it is particularly advantageous if the cosmetic compositions comprise at least one anionic surfactant a) and at least one amphoteric surfactant b) in a weight ratio a):b) of 10:1 to 1:3, more preferably of 7:1 to 1:2, and in particular of 5:1 to 1:1.

A fourth preferred embodiment of the use according to the invention is thus characterized in that the cosmetic compositions, in addition to spray-dried yoghurt powder, comprise
- a) at least one anionic surfactant in a weight fraction of 3 to 8 wt. %,
- b) spray-dried yoghurt powder in a weight fraction of 0.01 to 10 wt. %, and
- c) at least one cationic polymer in a weight fraction of 0.01 to 5 wt. %, wherein the quantity information is based on the total weight of the compositions.

Within the third and fourth preferred embodiments, it is furthermore particularly preferred for the cosmetic composition to be present in liquid form, and in particular in the form of a liquid soap, shower gel, shower bath, bubble bath, facial washing gel, peeling or facial toner.

Within the third and fourth preferred embodiments, the cosmetic composition preferably has a water content of at least 60 wt. %, more preferably of at least 70 wt. %, particularly preferably of at least 80 wt. %, and in particular of at least 85 wt. %, wherein the quantity information is based on the total weight of the cosmetic composition.

Preferably, the following surface-active substances are suitable anionic surfactants for the use according to the invention:
- ether carboxylic acids of formula $R—O—(CH_2—CH_2O)_x—CH_2—COOH$, in which R is a linear alkyl group having 8 to 30 carbon atoms, and x=0 or 1 to 16, and the salts thereof;
- acyl sarcosides having 8 to 24 carbon atoms in the acyl group;
- acyl taurides having 8 to 24 carbon atoms in the acyl group;
- acyl isethionates having 8 to 24 carbon atoms in the acyl group;
- sulfosuccinic acid monoalkyl and dialkyl esters having 8 to 24 carbon atoms in the alkyl group, and sulfosuccinic acid monoalkyl polyoxyethyl esters having 8 to 24 carbon atoms in the alkyl group and 1 to 6 oxyethyl groups;
- linear alkane sulfonates having 8 to 24 carbon atoms;
- linear alpha-olefin sulfonates having 8 to 24 carbon atoms;
- alpha-sulfo fatty acid methyl esters of fatty acids having 8 to 30 carbon atoms;
- alkyl sulfates and alkyl polyglycol ether sulfates of formula $R—O(CH_2—CH_2O)_x—SO_3H$, in which R is a preferably linear alkyl group having 8 to 30 carbon atoms, and x=0 or 1 to 12;
- hydroxysulfonates essentially corresponding to at least one of the following two formulas or the mixtures thereof and the salts thereof, $CH_3—(CH_2)_y—CHOH—(CH_2)_p—(CH—SO_3M)-(CH_2)_z—CH_2—O—(C_nH_{2n}O)^x—H$, and/or $CH_3—(CH_2)_y—(CH—SO_3M)-(CH_2)_p—CHOH—(CH_2)_z—CH_2—O—(C_nH_{2n}O)_x—H$, wherein in the two formulas y and z=0 or integers from 1 to 18, p=0, 1 or 2, and the sum (y+z+p) is a number from 12 to 18, x=0 or a number from 1 to 30, and n is an integer from 2 to 4, and M=H or alkali, in particular sodium, potassium, lithium, alkaline earth, in particular magnesium, calcium, zinc and/or an ammonium ion, which may optionally be substituted, in particular mono-, di-, tri- or tetra-ammonium ions having C1 to C4 alkyl, alkenyl or aryl groups;
- sulfated hydroxyalkyl polyethylene and/or hydroxyalkylenepropylene glycol ethers of formula $R^1—(CHOSO_3M)-CHR^3—(OCHR^4—CH_2)_n—OR^2$, where $R^1$ denotes a linear alkyl group having 1 to 24 carbon atoms, $R^2$ denotes a linear or branched, saturated alkyl group having 1 to 24 carbon atoms, $R^3$ denotes hydrogen or a linear alkyl group having 1 to 24 carbon atoms, $R^4$ denotes hydrogen or a methyl group, and M denotes hydrogen, ammonium, alkylammonium, alkanolammonium, in which the alkyl and alkanol groups each comprise 1 to 4 carbon atoms, or a metal atom selected from lithium, sodium, potassium, calcium or magnesium, and n denotes a number in the range from 0 to 12, and furthermore the total number of carbon atoms present in $R^1$ and $R^3$ is 2 to 44;
- sulfonates of unsaturated fatty acids having 8 to 24 carbon atoms and 1 to 6 double bonds;
- esters of tartaric acid and citric acid with alcohols that represent addition products of approximately 2 to 15 molecules ethylene oxide and/or propylene oxide to fatty alcohols having 8 to 22 carbon atoms;

alkyl and/or alkenyl ether phosphates of formula $R^1(OCH2CH2)_n$—O—(PO—OX)—$OR^2$,
in which $R^1$ preferably denotes an aliphatic hydrocarbon group having 8 to 30 carbon atoms, $R^2$ denotes hydrogen, a group $(CH2CH2O)_nR^2$ or X, n denotes numbers from 1 to 10, and X denotes hydrogen, an alkali metal or alkaline earth metal or $NR^3R^4R^5R^6$, where $R^3$ to $R^6$, independently of one another, denote hydrogen or a C1 to C4 hydrocarbon group;

sulfated fatty acid alkylene glycol esters of formula $RCO(alkO)_nSO_3M$ in which RCO— denotes a linear or branched, aliphatic, saturated and/or unsaturated acyl group having 6 to 22 carbon atoms, alk denotes $CH_2CH_2$, $CHCH_3CH_2$ and/or $CH_2CHCH_3$, n denotes numbers from 0.5 to 5, and M denotes a metal, such as alkali metal, in particular sodium, potassium, lithium, alkaline earth metal, in particular magnesium, calcium, zinc, or an ammonium ion, such as $^+NR^3R^4R^5R^6$, where $R^3$ to $R^6$ independently of one another denote hydrogen or a C1 to C4 hydrocarbon group;

monoglyceride sulfates and monoglyceride ether sulfates of formula $R^8OC$—$(OCH_2CH_2)_x$—$OCH_2$—[CHO$(CH_2CH_2O)_yH$]—$CH_2O(CH_2CH_2O)_z$—$SO_3X$, in which $R^8CO$ denotes a linear or branched acyl group having 6 to 22 carbon atoms, x, y and z in sum denote 0 or numbers from 1 to 30, preferably 2 to 10, and X denotes an alkali metal or alkaline earth metal. Typical examples of monoglyceride (ether) sulfates suitable within the meaning of the invention are the reaction products of lauric acid monoglyceride, coconut fatty acid monoglyceride, palmitic acid monoglyceride, stearic acid monoglyceride, oleic acid monoglyceride and tallow fatty acid monoglyceride, and the ethylene oxide adducts thereof with sulfur trioxide or chlorosulfonic acid in the form of the sodium salts thereof. Preferably, monoglyceride sulfates are used in which $R^8CO$ denotes a linear acyl group having 8 to 18 carbon atoms.

amide ether carboxylic acids, $R^1$—CO—$NR^2$—$CH_2CH_2$—O—$(CH_2CH_2O)_nCH_2COOM$, where $R^1$ denotes a straight-chain or branched alkyl or alkenyl group having a number of carbon atoms in the chain from 2 to 30, n denotes an integer from 1 to 20, and $R^2$ denotes hydrogen, a methyl, ethyl, propyl, isopropyl, n-butyl, t-butyl or iso-butyl group, and M denotes hydrogen or a metal such as alkali metal, in particular sodium, potassium, lithium, alkaline earth metal, in particular magnesium, calcium, zinc, or an ammonium ion, such as $^+NR^3R^4R^5R^6$, where $R^3$ to $R^6$ independently of one another denote hydrogen or a C1 to C4 hydrocarbon group. Such products are available from Chem-Y by the product designation Akypo®, for example.

acyl glutamates of formula XOOC—CH2CH2CH(C(NH)OR)—COOX, in which RCO denotes a linear or branched acyl group having 6 to 22 carbon atoms, and 0 and/or 1, 2 or 3 double bonds, and X denotes hydrogen, an alkali metal and/or alkaline earth metal, ammonium, alkyl ammonium, alkanol ammonium or glucammonium;

condensation products of a water-soluble salt of a water-soluble protein hydrolysate with a C8 to C30 fatty acid. Such products have been commercially available for quite some time under the trademark Lamepon®, Maypon®, Gluadin®, Hostapon®KCG or Amisoft®.

alkyl and/or alkenyl oligoglycoside carboxylates, -sulfates, -phospates and/or -isethionates, acyl lactylates; and hydroxy mixed ether sulfates,
and the mixtures thereof.

Preferred are mild anionic surfactants comprising polyglycol ether chains. To the extent that the mild anionic surfactants comprise polyglycol ether chains, it is especially particularly preferred for these to exhibit a restricted distribution of homologs. Furthermore, it is preferred in the case of mild anionic surfactants comprising polyglycol ether units for the number of the glycol ether groups to be 1 to 20, preferably 2 to 15, and particularly preferably 2 to 12. Particularly mild anionic surfactants comprising polyglycol ether groups exhibiting no restricted distribution of homologs can also be obtained, for example, when the number of the polyglycol ether groups is 4 to 12, and Zn or Mg ions are selected as the counterion. One example of this is the commercial product Texapon®.

Particularly preferred are:

acyl sarcosides having 8 to 24 carbon atoms in the acyl group;

ether carboxylic acids of formula R—O—$(CH_2$—$CH_2O)_x$—$CH_2$—COOH, in which R is a linear alkyl group having 8 to 30 carbon atoms, and x=0 or 1 to 16, and the salts thereof;

acyl taurides having 8 to 24 carbon atoms in the acyl group, acyl isethionates having 8 to 24 carbon atoms in the acyl group;

alkyl sulfates and alkyl polyglycol ether sulfates of formula R—$O(CH_2$—$CH_2O)_x$—$SO_3H$, in which R is a preferably linear alkyl group having 8 to 30 carbon atoms, and x=0 or 1 to 12;

alkyl and/or alkenyl ether phosphates of formula $R^1(OCH_2CH_2)_n$—O—(PO—OX)—$OR^2$, in which $R^1$ preferably denotes an aliphatic hydrocarbon group having 8 to 30 carbon atoms, $R^2$ denotes hydrogen, a group $(CH_2CH_2O)_nR^2$ or X, n denotes numbers from 1 to 10, and X denotes hydrogen, an alkali metal or alkaline earth metal or $NR^3R^4R^5R^6$, where $R^3$ to $R^6$, independently of one another, denote hydrogen or a $C_1$ to $C_4$ hydrocarbon group;

monoglyceride sulfates and monoglyceride ether sulfates of formula $R^8OC$—$(OCH_2CH_2)_x$—$OCH_2$—[CHO$(CH_2CH_2O)_yH$]—$CH_2O(CH_2CH_2O)_z$—$SO_3X$, in which $R^8CO$ denotes a linear or branched acyl group having 6 to 22 carbon atoms, x, y and z in sum denote 0 or numbers from 1 to 30, preferably 2 to 10, and X denotes an alkali metal or alkaline earth metal. Typical examples of monoglyceride (ether) sulfates suitable within the meaning of the invention are the reaction products of lauric acid monoglyceride, coconut fatty acid monoglyceride, palmitic acid monoglyceride, stearic acid monoglyceride, oleic acid monoglyceride and tallow fatty acid monoglyceride, and the ethylene oxide adducts thereof with sulfur trioxide or chlorosulfonic acid in the form of the sodium salts thereof. Preferably, monoglyceride sulfates are used in which $R^8CO$ denotes a linear acyl group having 8 to 18 carbon atoms.

acyl glutamates of formula XOOC—CH2CH2CH(C(NH)OR)—COOX, in which RCO denotes a linear or branched acyl group having 6 to 22 carbon atoms, and 0 and/or 1, 2 or 3 double bonds, and X denotes hydrogen, an alkali metal and/or alkaline earth metal, ammonium, alkyl ammonium, alkanol ammonium or glucammonium;

condensation products of a water-soluble salt of a water-soluble protein hydrolysate with a C8 to C30 fatty acid, and the mixtures thereof.

Especially particularly preferred are alkyl sulfates and alkylpolyglycol ether sulfates of formula R—O(CH$_2$—CH$_2$O)$_x$—SO$_3$H, in which R is a preferably linear alkyl group having 8 to 30 carbon atoms and x=0 or 1 to 12, and acyl glumates of formula XOOC—CH2CH2CH(C(NH)OR)—COOX, in which RCO denotes a linear or branched acyl group having 6 to 22 carbon atoms, and 0 and/or 1, 2 or 3 double bonds, and X denotes hydrogen, an alkali metal and/or alkaline earth metal, ammonium, alkyl ammonium, alkanol ammonium or glucammonium; and the mixtures thereof.

Most preferred are alkyl sulfates and alkylpolyglycol ether sulfates of formula R—O(CH$_2$—CH$_2$O)$_x$—SO$_3$H, in which R is a preferably linear alkyl group having 8 to 30 carbon atoms, particularly preferably having 8 to 24 carbon atoms, and in particular having 10 to 18 carbon atoms, and x denotes 0 or 1 to 12, preferably 1 to 6, and in particular 2 to 4, and the mixtures thereof.

The total amount of anionic surfactants in the cosmetic compositions of the third and fourth preferred embodiments is preferably 3 to 8 wt. %, more preferably 4 to 8 wt. %, particularly preferably 5 to 8 wt. %, and in particular 5.5 to 8%, wherein the quantity information is based on the total weight of the cosmetic compositions.

Particularly suited zwitterionic surfactants for the use according to the invention are those known as betaines, such as N-alkyl-N,N-dimethylammonium glycinates, for example coconut alkyl dimethylammonium glycinate, N-acylaminopropyl-N,N-dimethylammonium glycinate, for example, coconut acylaminopropyl dimethylammonium glycinate, and 2-alkyl-3-carboxymethyl-3-hydroxyethyl imidazolines, each having 8 to 18 carbon atoms in the alkyl or acyl group, and coconut acylamino ethylhydroxyethyl carboxymethyl glycinate. A preferred zwitterionic surfactant is the fatty acid amide derivative known by the INCI name Cocamidopropyl Betaine, and Coco Betaine.

Ampholytic surfactants shall be understood to mean those surface-active compounds capable of forming inner salts. Examples of suitable ampholytic surfactants are N-alkyl glycines, N-alkylpropionic acids, N-alkylaminobutytic acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids, each having approximately 8 to 24 carbon atoms in the alkyl group. Typical examples of amphoteric or zwitterionic surfactants are alkyl betaines, alkyl amido betaines, aminopropionates, amino glycinates, imidazolinium betaines and sulfobetaines.

Particularly preferred ampholytic surfactants are N-cocoalkylaminopropionate, cocoacylaminoethyl aminopropionate, the fatty acid amide derivative known by the INCI name Cocamidopropyl Betaine, and C$_{12}$ to C$_{18}$ acyl sarcosine.

The total amount of amphoteric and/or zwitterionic surfactants in the cosmetic compositions of the third and fourth preferred embodiments is preferably 1 to 6 wt. %, more preferably 1.2 to 5 wt. %, particularly preferably 1.4 to 4.5 wt. %, and in particular 1.5 to 4%, wherein the quantity information is based on the total weight of the cosmetic compositions.

Suitable cationic polymers are, for example:
quaternized cellulose derivatives, in particular Polyquaternium-10, as they are commercially available under the designations Celquat® and Polymer JR®;
hydrophobically modified cellulose derivatives, for example the cationic polymers sold under the trade name SoftCat®;
cationic alkyl polyglycosides;
cationized honey, for example the commercial product Honeyquat® 50;
cationic guar derivatives, such as in particular the products sold under the trade names Cosmedia®Guar N-Hance® and Jaguar®;
polymeric dimethyl diallyl ammonium salts and the copolymers thereof with esters and amides of acrylic acid and methacrylic acid, especially Polyquaternium-6 and Polyquaternium-7. The products available commercially under the designations Merquat 100 (poly(dimethyldiallylammonium chloride)) and Merquat® 550 (dimethyldiallylammonium chloride/acrylamide copolymer) are examples of such cationic polymers;
copolymers of vinylpyrrolidone with quaternized derivatives of dialkyl aminoalkyl acrylate and methacrylate, such as diethyl sulfate-quaternized vinylpyrrolidone/dimethylaminoethyl methacrylate copolymers. Such compounds are commercially available under the designations Gafquat®734 and Gafquat® 755;
vinylpyrrolidone/vinylimidazolium methochloride copolymers, as they are offered under the designations Luviquat® FC 370, FC 550, FC 905 and HM 552;
quaternized polyvinyl alcohol;
and the polymers known by the designations
Polyquaternium 2, Polyquaternium 17, Polyquaternium 18, Polyquaternium-24, Polyquaternium 27, Polyquaternium-32, Polyquaternium-37, Polyquaternium 74, and Polyquaternium 89.

Preferred cationic polymers are quaternized cellulose polymers, cationic guar derivatives and/or cationic polymers based on acrylic acid (derivatives), which particularly preferably are selected from the polymers known by the INCI names Guar Hydroxypropyltrimonium Chloride, Polyquaternium-6, Polyquaternium-7, Polyquaternium-10, Polyquaternium-37 and/or Polyquaternium-67. The cationic polymers known by the INCI name Polyquaternium-7 are in particular preferred for use in the cosmetic compositions to be used according to the invention.

The cationic polymer or polymers can preferably be used in the cosmetic compositions to be used according to the invention in a weight fraction (based on the total weight of the cosmetic compositions) of 0.01 to 5 wt. %, more preferably of 0.02 to 4 wt. %, particularly preferably of 0.05 to 3 wt. %, and in particular of 0.1 to 2 wt. %.

A second subject matter of the present invention relates to a prebiotically active cosmetic composition comprising
a) at least one fatty acid soap in a weight fraction of 10 to 75 wt. %, preferably 15 to 70 wt. %, particularly preferably 20 to 65 wt. %, and in particular 25 to 60 wt. %, and
b) spray-dried yoghurt powder in a weight fraction of 0.01 to 10 wt. %, preferably 0.02 to 7.5 wt. %, particularly preferably 0.03 to 5 wt. %, and in particular 0.05 to 3 wt. %,
wherein the quantity information is based on the total weight of the cosmetic composition.

What was said with respect to the use according to the invention applies, mutatis mutandis, with respect to preferred embodiments of the composition according to the invention.

In a first preferred embodiment of the second subject matter of the invention, the prebiotically active cosmetic compositions are present in a solid consistency. In this embodiment, these preferably comprise water in a weight fraction of 0.1 to 20 wt. %, more preferably of 5 to 18 wt. %, and particularly preferably of 7.5 to 17.5 wt. %, wherein the quantity information is based on the total weight of the cosmetic composition.

In a second preferred embodiment, the prebiotically active cosmetic compositions have an alkaline pH value, which is preferably in the range of 8 to 12, more preferably of 9 to 12, particularly preferably of 9.5 to 11.5, and in particular of 10 to 11.

In a third preferred embodiment of the second subject matter of the invention, the prebiotically active cosmetic compositions comprise the sodium salt(s) of tallow fatty acid (INCI name: Sodium Tallowate), of coconut fatty acid (INCI name: Sodium Cocoate), of olive oil fatty acid (INCI name: Sodium Olivate), of palm oil fatty acids (INCI name: Sodium Palmate), of lard fatty acids (INCI names: Sodium Lardate) and/or of palm kernel oil fatty acids (INCI name: Sodium Palm Kernelate) as particularly preferred fatty acid soap(s).

It may be in particular of advantage if the cosmetic compositions within this embodiment comprise mixtures of the above-mentioned fatty acid soaps.

In a further preferred embodiment, the spray-dried yoghurt powder in the prebiotically active cosmetic composition of the second subject matter of the invention comprises proteins.

It is particularly preferred for the spray-dried yoghurt powder to comprise proteins in a weight fraction of 20 to 30%, more preferably 22 to 28%, particularly preferably 24 to 26%, and in particular of approximately 25%, wherein the quantity information is based on the total weight of the spray-dried yoghurt powder.

From an application point of view, it has proven advantageous for the prebiotically active cosmetic compositions of the second subject matter of the invention to have a certain content of free, unsaponified fatty acids in addition to the fatty acid soap(s). The content of free fatty acids allowed in particular the foaming and foam properties to be improved. In particular, a creamy foam having fine bubbles was obtained, which leaves behind a pleasant sensation on the skin.

In a fourth preferred embodiment, the prebiotically active cosmetic compositions of the second subject matter of the invention thus furthermore comprise free fatty acids, wherein the weight fraction of the free fatty acids in the total weight of the cosmetic compositions is preferably 0.01 to 10 wt. %, more preferably 0.1 to 8 wt. %, particularly preferably 0.25 to 6 wt. %, and in particular 0.5 to 5 wt. %.

One particularly preferred active ingredient, which may furthermore be present in the prebiotically active cosmetic compositions of the second subject matter of the invention, is talc. It was found that talc, in combination with spray-dried yoghurt powder and at least one fatty acid soap, improves the suppleness of the skin and skin moisture.

Talc within the meaning of the invention shall be understood to mean a hydrated magnesium silicate of the theoretical composition $3MgO.4SiO_2.H_2O$ or $Mg_3(Si_4O_{10}).(OH)_2$, which, however, may comprise fractions of hydrated magnesium aluminum silicate of up to 12 wt. % $Al_2O_3$, based on the total product.

The particle diameter (equivalent spherical diameter) of the talc should preferably range between 0.5 and 50 µm. In general, talc qualities comprising no more than 5 wt. % of particles below 1 µm and no more than 5 wt. % of particles above 50 µm in size have proven useful. The fraction of particles that, on average, are greater than 40 µm (sieve retention) is preferably no more than 2 wt. %. The average particle diameter (D 50) is preferably 5 to 15 µm.

The content of by-products should preferably not account for more than 1.6 wt. % $Fe_2O_3$, 1 wt. % CaO and 1 wt. % unbound water (loss in drying at 105° C.). The content of hydrated magnesium aluminum silicate can be as much as 60 wt. %, calculated as $Al_2O_3$, to 12 wt. %.

In a fifth preferred embodiment, the prebiotically active compositions of the second subject matter of the invention furthermore comprise talc, wherein the weight fraction of the talc in the total weight of the cosmetic compositions is preferably 1 to 40 wt. %, more preferably 2 to 30 wt. %, particularly preferably 3 to 25 wt. %, and in particular 5 to 20 wt. %.

In addition to the above-mentioned active ingredients, the prebiotically active cosmetic compositions of the second subject matter of the invention can comprise further active ingredients, which impart advantageous properties to these, such as improved mildness and improved nourishing properties.

The preferred further active ingredients that may be used in the prebiotically active cosmetic compositions of the second subject matter of the invention include, for example:
  non-ionic surfactants and/or non-ionic emulsifiers, which can preferably be used in a weight fraction of 0.01 to 5 wt. %, more preferably of 0.05 to 4 wt. %, and in particular of 0.1 to 3 wt. %, based on the total weight of the cosmetic composition, and
  active ingredients positively influencing skin moisture, which can preferably be used in a weight fraction of 0.001 to 10 wt. %, more preferably of 0.005 to 7.5 wt. %, particularly preferably of 0.01 to 5 wt. %, and in particular of 0.02 to 4 wt. %, based on the total weight of the cosmetic composition.

Suitable non-ionic surfactants/emulsifiers include, for example,
  amine oxides;
  addition products of 2 to 50 moles ethylene oxide and/or 0 to 5 moles propylene oxide to linear and branched fatty alcohols having 8 to 30 carbon atoms, to fatty acids having 8 to 30 carbon atoms, and to alkyl phenols having 8 to 15 carbon atoms in the alkyl group;
  addition products of 5 to 60 moles ethylene oxide to castor oil and/or hydrogenated castor oil;
  sugar fatty acid esters and addition products of ethylene oxide to sugar fatty acid esters;
  fatty acid alkanolamides;
  addition products of ethylene oxide to fatty amines and/or alkyl polyglucosides.

Particularly suitable non-ionic surfactants/emulsifiers are alkyl oligoglucosides, and in particular alkyl oligoglucosides based on hydrogenated $C_{12/14}$ coconut alcohol having a DP of 1 to 3, as they are commercially available by the INCI name "Coco-Glucoside," for example.

Further preferred non-ionic surfactants/emulsifiers are addition products of 5 to 60 moles ethylene oxide to castor oil and/or hydrogenated castor oil, such as the emulsifiers known by the INCI names PEG-40 Hydrogenated Castor Oil and/or PEG-60 Hydrogenated Castor Oil.

Suitable active ingredients that positively influence skin moisture shall preferably be understood to mean at least one active ingredient that is selected from the following group:
  i. glycerol,
  ii. vitamins,
  iii. cationic polymers and/or
  iv. plant extracts, milks and/or juices.

Glycerol can preferably be used in the prebiotically active cosmetic compositions of the second subject matter of the invention in a weight fraction of 0.1 to 10 wt. %, more preferably 0.2 to 8 wt. %, particularly preferably 0.5 to 5 wt. %, and in particular 1 to 5 wt. %, wherein the quantity information is based on the total weight of the cosmetic compositions.

Suitable vitamins shall preferably be understood to mean the following vitamins, provitamins, and vitamin precursors, and the derivatives thereof:

Vitamin A: The group of substances referred to as vitamin A includes retinol (vitamin $A_1$) and 3,4-didehydroretinol (vitamin $A_2$). β-carotene is the provitamin of retinol. Possible vitamin A components are, for example, vitamin A acid and the esters thereof, vitamin A aldehyde, and vitamin A alcohol and the esters thereof, such as palmitate and acetate.

Vitamin B: The vitamin B group or vitamin B complex includes, among other things, Vitamin $B_1$ (thiamine)

Vitamin $B_2$ (riboflavin)

Vitamin $B_3$. The compounds nicotinic acid and nicotinic acid amide (niacinamide) are often covered by this designation Vitamin $B_5$ (pantothenic acid and panthenol). Within this group, panthenol is preferably used. Derivatives of panthenol that may be used are in particular the esters and ethers of panthenol and cationically derivatized panthenols. Individual representatives are, for example, panthenol triacetate, panthenol monoethyl ether and the monoacetate thereof, and cationic panthenol derivatives Vitamin $B_6$ (pyridoxine, pyridoxamine and pyridoxal);

Vitamin C (ascorbic acid): Use in the form of the palmitic acid ester, glucosides or phosphates can be preferred. Use in combination with tocopherols can likewise be preferred;

Vitamin E (tocopherols, in particular α-tocopherol);

Vitamin F: The term "Vitamin F" is usually understood to mean essential fatty acids, in particular linoleic acid, linolenic acid and arachidonic acid;

Vitamin H: Vitamin H refers to the compound (3aS,4S,6aR)-2-oxohexahydrothienol[3,4-d]-imidazole-4-valeric acid, although this has since become established by the trivial name biotin.

The prebiotically active cosmetic compositions of the second subject matter of the invention can preferably comprise vitamins, provitamins and vitamin precursors from the groups A, B, E and H. Vitamins, provitamins and vitamin precursors from group B are particularly preferred; in particular, nicotinic acid amide and/or panthenol are preferred.

Vitamins, vitamin derivatives and/or vitamin precursors may preferably be used in the agents according to the invention of the second subject matter of the invention (based on the total weight of the agents) in an amount of 0.001 to 2 wt. %, particularly preferably of 0.005 to 1 wt. %, and in particular of 0.01 to 0.5 wt. %. Suitable cationic polymers and the amounts thereof used were disclosed earlier in the description.

Suitable plant extracts, milks and/or juices that may be present in the cosmetic cleansing agents according to the invention can preferably be selected from green tea, oak bark, stinging nettle, witch hazel, hops, henna, chamomile, burdock root, horsetail, hawthorn, lime blossom, almond, aloe vera, pine needle, horse chestnut, sandalwood, juniper, coconut, mango, apricot, lime, wheat, kiwi, melon, orange, grapefruit, sage, rosemary, birch, mallow, lady's smock, creeping thyme, yarrow, thyme, balm, restharrow, coltsfoot, vanilla, marshmallow, meristem, ginseng, and ginger root.

Extracts of green tea, almond, aloe vera, coconut, mango, apricot, lime, wheat, vanilla, kiwi and melon are particularly preferred, and in particular the extracts of aloe vera, coconut, vanilla and melon are preferred.

The extracts are usually produced by way of extraction of the entire plant. However, in isolated cases, it may also be preferred to produce the extracts exclusively from flowers and/or leaves of the plant.

Extracting agents for producing the described plant extracts that may be used are water, alcohols and the mixtures thereof. Among the alcohols, lower alcohols, such as ethanol and isopropanol, in particular, however, polyhydric alcohols, such as ethylene glycol and propylene glycol, both as the sole extracting agent and also in a mixture with water, are preferred. Plant extracts based on water/propylene glycol at a ratio of 1:10 to 10:1 have proven to be particularly suitable.

The plant extracts can be used either in pure form or in dilute form. If they are used in dilute form, they usually contain approximately about 2 to 80 wt. % active substance and, as solvent, the extracting agent or extracting agent mixture used during extraction thereof.

Aloe milk, aloe vera leaf juice and coconut milk may preferably be used as the plant milk or juice. The plant milks/juices can preferably be used in the cosmetic compositions of the second subject matter of the invention in a weight fraction of 0.01 to 5 wt. %, preferably 0.02 to 4 wt. %, and in particular 0.05 to 3 wt. %, based on the total weight of the agent.

In a sixth preferred embodiment, the prebiotically active cosmetic compositions of the second subject matter of the invention furthermore comprise at least one active ingredient c) positively influencing skin moisture in a weight fraction of 0.01 to 10 wt. %, preferably 0.05 to 7.5 wt. %, more preferably 0.1 to 5 wt. %, and in particular 0.2 to 4 wt. %, wherein the quantity information is based on the total weight of the compositions, and wherein the active ingredient is selected from
  i. glycerol,
  ii. vitamins,
  iii. cationic polymers and/or
  iv. plant extracts, milks and/or juices.

Within this embodiment, it is particularly preferred for the active ingredient c) to be selected from glycerol, panthenol, niacinamide, a cationic polymer known by the INCI name Polyquaternium-10, a cationic polymer known by the INCI name Polyquaternium-7 and/or extracts, milks and/or juices of aloe vera (Aloe barbadensis) and/or of coconut. In particular, niacinamide, Polyquaternium-7, aloe milk and/or coconut milk are preferred.

Further active ingredients, auxiliary substances and additives are, for example:

cosmetic ingredients for soaps, for example as disclosed in "Soaps and Detergents", Luis Spitz, ISBN 0-935315-72-1, and "Production of Toilet Soap", D. Osteroth, ISBN 3-921956-55-2;

thickening agents such as agar-agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as bentonite or fully synthetic hydrocolloids, such as polyvinyl alcohol;

dimethyl isosorbide and cyclodextrins;

anti-dandruff active ingredients such as piroctone olamine, zinc omadine, and climbazole;
active ingredients such as allantoin and bisabolol;
complexing agents such as EDTA, tetrasodium etidronate, NTA, β-alaninediacetic acid, iminodisuccinic acid and the salts thereof, and phosphonic acids;
swelling and penetration substances such as primary, secondary and tertiary phosphates;
opacifiers, such as latex, styrene/PVP and styrene/acrylamide copolymers;
pearlizing agents such as ethylene glycol monostearate and distearate and PEG-3 distearate;
pigments;
antioxidants;
menthol and menthol derivatives;
inorganic salts such as alkali sulfates and/or chlorides;
organic salts such as alkali metal lactates;
dyes, and
perfumes.

The production of the prebiotically active cosmetic compositions in a solid consistency can take place in a manner customary for such products, wherein in particular the active ingredient combination according to the invention creates an easily moldable mass that when exposed to heat is sufficiently plastic, but not rubber-elastic, and that is solid after cooling, and wherein the shaped products have a smooth surface. Conventional methods for mixing or homogenizing, kneading, optionally refining, extrusion molding, optionally pelletizing, extruding, cutting and bar pressing are known to a person skilled in the art and may be used to produce the bar soaps according to the invention. Production is preferably carried out in a temperature range of 40 to 90° C., wherein the meltable charged substances are introduced into a heatable kneader or mixer, and the non-melting components are stirred in. The mixture may subsequently be passed through a sieve for homogenization before it is then molded. In a preferred embodiment of the invention, the components are used in anhydrous, granular form, as they are obtained after drying in what is known as a flash dryer. Reference shall be made in this regard to the teaching of German patent specification DE 19534371 C1.

Shaped soap products, however, may also be present in the form of noodles, needles, granules, extrudates, flakes and in any other form common for soap products.

Furthermore, the bars of soap may be imparted a marbled appearance, for example by injecting dye solutions during the extrusion process.

Likewise, the bars of soap can be processed as multi-phase soaps, in particular also as bars of soap provided with a nourishing phase.

Finally, the bars of soap may even exhibit a certain transparency. For this purpose, the inorganic components are selected to be especially fine. It is then possible to obtain at least semi-transparent soaps.

EXAMPLES

1) Prebiotic Effect of the Active Ingredient Combinations
a) spray-dried yoghurt powder and anionic surfactant(s) and fatty acid soap(s)
b) spray-dried yoghurt powder and fatty acid soap(s)

The test was carried out to demonstrate the prebiotic action in cosmetic compositions comprising the above-mentioned active ingredient combinations. The "prebiotic effect" shall be understood to mean the difference between the quantitative number of desirable bacteria (*S. epidermis*) and the number of undesirable bacteria (*Propionibacterium acnes*) at two different points in time. For a prebiotic effect to be present, a difference in favor of the desirable bacteria must be shown.

The following compositions were analyzed (the quantity information is based on [% by weight]):

|  | Shower gel | Liquid soap | Solid soap |
|---|---|---|---|
| Sodium laureth sulfate | 5.60 | 7.70 |  |
| Cocamidopropyl betaine | 3.80 | 1.50 |  |
| PEG-7 Glyceryl Cocoate | 0.40 | 0.30 |  |
| Styrene/Acrylates Copolymer | 0.30 | 0.30 |  |
| Polyquaternium-7 | 0.27 |  |  |
| Laureth-2 | 0.15 |  |  |
| Yoghurt Protein GBU ®[1] | 0.05 | 0.05 | 0.05 |
| Niacinamide |  | 0.01 | 0.01 |
| Perfume | 0.70 | 0.70 | 0.70 |
| Citric acid | 0.40 | 0.30 |  |
| Sodium benzoate, sodium salicylate | q.s. | q.s. |  |
| Sodium chloride | 0.75 | 2.00 | 0.25 |
| Sodium tallowate |  |  | 47.50 |
| Talc |  |  | 18.00 |
| Sodium cocoate |  |  | 11.00 |
| Glycerol |  |  | 2.80 |
| Dolomita |  |  | 2.00 |
| Coconut acid |  |  | 0.50 |
| Tallow acid |  |  | 0.50 |
| PEG-450 |  |  | 0.25 |
| Sodium lactate |  |  | 0.07 |
| *Aloe barbadensis* leaf juice |  | 0.01 | 0.01 |
| Dyes |  |  | q.s. |
| Water | to make up 100 | to make up 100 | to make up 100 |

The growth of *S. epidermis* (DSMZ 20042) and *Propionibacterium acnes* (DSMZ 1897) on 3 membranes (0.8 to 3.1×10⁶ cfu) was analyzed. After the bacteria was left on the surfaces of the 3 membranes for 3 hours under aerobic conditions (37° C.), each membrane was applied to the respective test product (200 μL; heated to 37° C.). Contact was established for 2 minutes between the respective product and the particular membrane, and thereafter the membranes were each washed twice with 2 mL water each. Thereafter, the number of bacteria remaining on the three membranes was directly determined. After having then incubated membranes for 24 hours at 37° C., the above-described method was repeated twice more.

Figure 2:
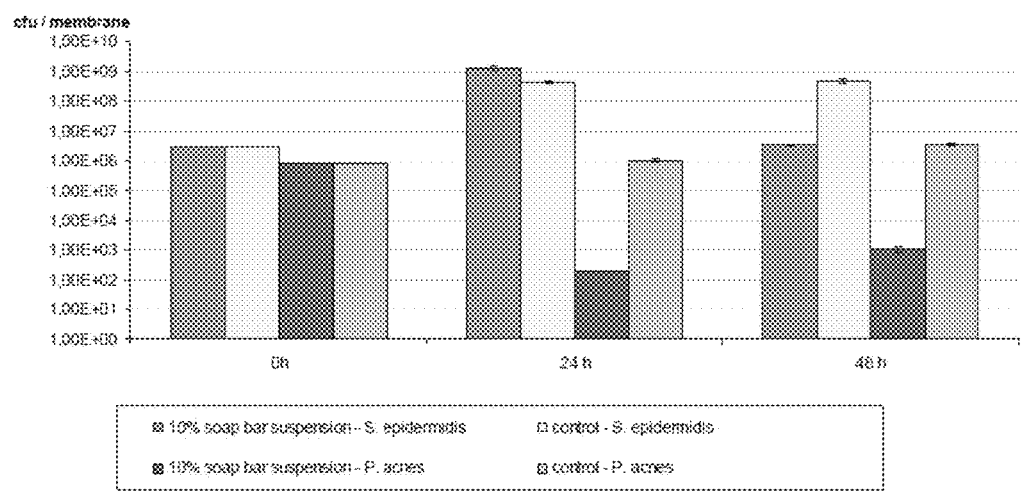
FIG. 2 is a bar graph depicting data for the prebiotic efficacy of a bar soap formulation according to the present invention compared to a control (water).

The results are shown in the diagrams in FIGS. 1 and 2.

Further Exemplary Embodiments

The following soaps were produced (unless indicated otherwise, the quantity information is based on % by weight):

| | 1 | 2 | 3 | 4 | 5 | 6 | 7 | 8 | 9 | 10 |
|---|---|---|---|---|---|---|---|---|---|---|
| Sodium tallowate | 47.6 |  |  | 25 | 50 | 50 |  | 45 | 45 |  |
| Sodium olivate |  |  | 80 |  |  |  |  |  |  |  |

-continued

|  | 1 | 2 | 3 | 4 | 5 | 6 | 7 | 8 | 9 | 10 |
|---|---|---|---|---|---|---|---|---|---|---|
| Sodium Palmate |  | 47.6 |  |  |  |  | 50 |  |  | 45 |
| Sodium lardate |  |  |  | 25 |  |  |  |  |  |  |
| Sodium sulfate |  |  |  |  | 4 |  |  |  |  |  |
| CAPB |  |  |  |  |  |  | 3 |  |  |  |
| Talc | 20 | 20 | 5 | 15 | 10 | 10 | 5 | 10 | 10 | 20 |
| Polyquaternium-7 |  |  |  |  |  |  |  | 0.3 |  |  |
| Coco glucoside |  |  |  |  |  |  |  |  | 2 |  |
| Corn starch |  |  |  |  |  |  | 5 |  | 5 |  |
| Sodium cocoate | 10 |  |  | 20 | 10 | 20 |  | 30 | 23 | 20 |
| Sodium palm kernelate |  | 10 |  |  |  |  | 20 |  |  |  |
| Glycerol | 3 | 3 | 1 |  | 4 |  | 2 |  |  |  |
| Perfume | 0.8 | 1 | 2 | 2 | 1 | 1.5 | 1 | 0.5 | 1 | 1 |
| Coconut acid | 0.5 |  |  |  |  | 3 |  | 1.5 | 1.5 |  |
| Palm kernel oil fatty acid |  | 0.5 |  |  |  |  | 1 |  |  |  |
| Tallow fatty acid | 0.5 |  |  |  | 2.5 | 3 |  | 1.5 | 1.5 |  |
| Palm oil fatty acid |  | 0.5 |  |  |  |  | 1 |  |  |  |
| PEG-450 | 0.3 |  |  |  | 0.5 |  |  |  |  |  |
| NaCl | 0.2 | 0.3 | 0.5 | 0.3 | 0.3 | 03 | 0.3 | 0.2 | 0.3 | 0.5 |
| Sodium lactate | 0.1 |  |  |  | 0.5 |  | 0.1 |  |  | 0.1 |
| BHT | 0.07 | 0.73 | 0.1 |  |  | 0.1 | 0.05 | 0.05 | 0.05 | 0.05 |
| Yoghurt powder | 0.05 | 0.5 | 0.2 | 0.05 | 0.1 | 0.7 | 0.1 | 0.15 | 0.1 | 0.1 |
| Na4 editronate | 0.02 | 0.2 |  | 0.02 | 0.3 | 0.1 |  | 0.1 | 0.1 | 0.05 |
| Na4 EDTA | 0.02 | 0.2 |  | 0.02 | 0.3 | 0.1 | 0.1 | 0.1 | 0.1 | 0.05 |
| Niacinamide | 0.01 | 0.1 |  |  |  |  |  |  |  |  |
| *Aloe barbadensis* leaf juice | 0.01 | 0.1 | 0.15 | 0.05 |  |  | 0.2 |  |  |  |
| Water | to make up 100 | to make up 100 | to make up 100 | to make up 100 | to make up 100 | to make up 100 | to make up 100 | to make up 100 | to make up 100 | to make up 100 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for inhibiting the growth and/or the physiological activity of undesirable skin bacteria and/or for preserving desirable skin bacteria, comprising applying to the skin of a subject in need thereof a prebiotically active cosmetic composition, wherein the cosmetic composition comprises:
   an effective amount of a spray-dried yoghurt powder;
   at least one anionic surfactant;
   10 to 75 wt. % of at least one fatty acid soap; and
   0.01 to 10 wt. % of at least one unsaponified free fatty acid,
   wherein said wt. % are based on the total weight of the cosmetic composition.

2. The method according to claim 1, wherein the prebiotically active cosmetic composition is conducive to the growth of coagulase-negative staphylococci while inhibiting the growth of *Propionibacterium acnes*.

3. The method according to claim 1, wherein the prebiotically active cosmetic composition is conducive to the growth of *S. epidermidis* or *S. warneri*.

4. The method according to claim 1, wherein prebiotically active cosmetic composition is applied to facial skin and/or on the skin on the neck, décolleté, back and/or on the arms.

5. The method according to claim 1, wherein the at least one anionic surfactant is in a weight fraction of 3 to 8 wt. %; and wherein the cosmetic composition further comprises at least one amphoteric and/or zwitterionic surfactant in a weight fraction of 1 to 6 wt. %, wherein said wt. % are based on the total weight of the cosmetic composition.

6. The method according to claim 1, wherein the at least one anionic surfactant is in a weight fraction of 3 to 8 wt. %, and the spray-dried yoghurt powder is in a weight fraction of 0.01 to 10 wt. %; and wherein the cosmetic composition further comprises at least one cationic polymer in a weight fraction of 0.01 to 5 wt. %,
   wherein said wt. % are based on the total weight of the cosmetic composition.

\* \* \* \* \*